United States Patent [19]

Stautzenberger et al.

[11] Patent Number: 4,766,236

[45] Date of Patent: Aug. 23, 1988

[54] PURIFICATION OF DIPHENYL PHTHALATES

[75] Inventors: A. Lee Stautzenberger; Ellen A. Langford, both of Nueces, Tex.

[73] Assignee: Hoechst Celanese Corporation, Chatham, N.J.

[21] Appl. No.: 68,584

[22] Filed: Jun. 30, 1987

[51] Int. Cl.$^4$ ............................................. C07C 67/48
[52] U.S. Cl. ......................................................... 560/78
[58] Field of Search .......................................... 560/78

[56] References Cited

U.S. PATENT DOCUMENTS 3,382,271  5/1968  McNerney .......................... 560/78
3,705,186  12/1972  Naskar ................................ 560/78

FOREIGN PATENT DOCUMENTS 511070   8/1939  United Kingdom ................. 560/78
2079752  1/1982  United Kingdom ................. 560/78

Primary Examiner—Paul J. Killos
Attorney, Agent, or Firm—DePaoli & O'Brien

[57] ABSTRACT

Color properties of crude phenolic esters of aromatic dicarboxylic acids are improved by distilling the esters in the presence of a boron oxide compound.

4 Claims, No Drawings

PURIFICATION OF DIPHENYL PHTHALATES

BACKGROUND OF THE INVENTION

1. Field of the Invention

The present invention relates to the purification of phenolic esters of aromatic carboxylic acids and more particularly to the purification of diphenyl esters of aromatic carboxylic acids, such as phthalic acid, isophthalic acid, etc., to provide esters monomer having good color properties.

2. Description of the Prior Art

The production of various phenolic esters of aromatic benzenedicarboxylic acids, such as diphenyl terephthalate and monophenyl terephthalate, have become of significant commercial interest in recent years due to their use in a great many types of processes. As an example, diphenyl terephthalate and diphenyl isophthalate when dissolved in a solvent may be reacted with a primary diamine to produce polyamides. Likewise, 3,3'-diaminobenzidine may be condensed with various diphenyl esters to form polybenzimidazoles. In the synthesis of polyarylate resins, such as Durel ®, a mixture of iso- and terephthalates is reacted with bisphenol A to provide resins which are of significant commercial interest. These esters may be produced by reaction of acid chlorides with a phenol to produce the phenyl ester and hydrogen chloride as a by-product, or by reacting a phenolic compound and aromatic dicarboxylic acid in the presence of a catalyst consisting of an alkali metal compound and a boron compound. While such processes are effective for producing phenolic esters they suffer the disadvantage that during the process of esterification, the ester acquires a pink to dark brown color which present methods of purification, such as vacuum distillation, recrystallization and/or carbon treatment, are insufficient to remove. Accordingly, there is a need for additional purification methods which are sufficient to achieve specification grade diphenyl phthalates.

U.S. Pat. No. 2,197,546 discloses color improvement of phthalic acid esters such as dibutyl, dihexyl, dioctyl, etc., phthalates, by heating the ester with salts of perboric acid at reflux under reduced pressure followed by separation of the ester by filtration. U.S. Pat. No. 2,780,643 discloses catalytic hydrogenation of synthetic alcohols for color improvement, followed by esterification of the alcohol with phthalic acid. U.S. Pat. No. 3,597,470 discloses purification of bis(2-hydroxyethyl) terephthalate for color improvement by contacting the terephthalate with a solution of sodium borohydride or diborane followed by crystallization and separation. U.S. Pat. No. 4,118,582 discloses purification of spent recycle ethylene glycol, recovered from polyethylene terephthalate manufacture, by adding an organic acid (e.g., acetic acid) and an alkali metal borohydride in the absence of oxygen to precipitate antimony oxide which is used as a catalyst in preparing the polyethylene terephthalate. U.S. Pat. No. 4,271,311 discloses esterification of phenol by reaction of a phenolic compound and a carboxylic acid in the presence of a catalyst consisting of an alkali metal compound and a boron compound selected from the group of boric acid, boric anhydride, alkali metal polyborates, alkali metal salts of boric acid and alkali metal borohydrides.

SUMMARY OF THE INVENTION

The present invention is directed to the improvement of color properties in phenolic esters of aromatic carboxylic acids, especially the diphenyl esters, by subjecting such esters to distillation in the presence of a boron compound.

DESCRIPTION OF THE INVENTION

In carrying out the invention crude diphenyl esters such as diphenyl phthalate, diphenyl isophthalate, etc., are contacted with an inorganic boron compound in amounts ranging from about 0.1 to 10.0 weight percent, based on the weight of the crude phenolic ester. The treatment with the boron compound is carried out after an esterification reaction mixture is formed as a result of esterifying an aromatic carboxylic acid with a phenol. Initially, the crude phenolic ester reaction mixture is treated with a basic substance, such as sodium hydroxide, potassium hydroxide, sodium carbonate, potassium carbonate, sodium bicarbonate, potassium bicarbonate, etc., to neutralize unreacted acid and partial esters in the esterification reaction mixture. This may be accomplished before the reaction mixture is contacted with the boron compound or may be accomplished concurrently with the contacting of the crude reaction mixture with the boron compound. Distillation is then carried out in a conventional manner under reduced pressure, less than atmospheric pressure, to reduce the color properties to a desired level. With previously prepared phthalate esters such as diphenyl phthalate, diphenyl isophthalate, or mixtures thereof, e.g., a phthalate ester prepared from phenol and a 3/1 mixture of iso- and terephthalic acid in the presence of a titanate catalyst, the ester usually has been initially purified by vacuum distillation but is distilled again in the presence of the boron compound. Prior to treatment with boron, esters of this type usually have a color of 200 to 500 APHA. Depending upon the crude ester type and its resistance to purification, one or more distillations in the presence of boron may be desirable.

The treatment and distillation with boron can be carried out at a temperature of about 225° C. to 260° C. under subatmospheric pressure of about 0.5 to 3 torr.

The boron compounds used for purposes of the invention are oxides of boron such as $H_3BO_3$ and $B_2O_3$. Other useful boron compounds include anhydrous borax (disodium tetraborate), Colemanite ($2\,CaO.3\text{-}B_2O_3.5H_2O$) and Ulexite ($NaCaB_5O_9.8H_2O$). The amount of boron compound may range from 1.0 to 10.0 weight percent, based on the crude ester, and is preferably about 1 to 5 weight percent. While the mechanism of the present invention is not clearly understood, it is believed that the boron oxides form adducts with color impurities, such as aldehydic and unsaturated chromogens, which do not distill over with the phenolic esters.

The esters are derived from aromatic carboxylic acids which should be essentially free of aldehydic and ketonic carbonyl groups as these groups interfere with the esterification reaction. Other than these aldo and keto groups, the aromatic carboxylic acid may contain various functional groups which do not interfere with the esterification reaction. Generally the aromatic carboxylic acid will contain no functional groups or radicals other than carboxyl, carboxylic ester, ether, thioether, aromatic ring-substituted halo, sulfo, or sulfonyl. The aromatic carboxylic acids which are free of ketonic and aldehydic carbonyl groups have the formula:

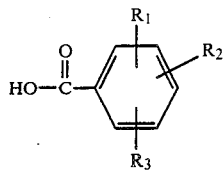

wherein $R_1$ and $R_2$ are alike or different and correspond to hydrogen, carboxyl or hydroxyl and wherein $R_3$ is hydrogen or an organic radical of six to 20 carbon atoms containing an aromatic ring, which organic radical is composed only of elements selected from the groups consisting of carbon, hydrogen, and oxygen.

Especially preferred are those dicarboxylic acids of the formula

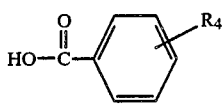

where $R_4$ is carboxyl group or a radical of seven to 20 carbon atoms of the formula

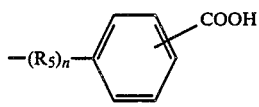

wherein n is 0 or 1 and $R_5$ is a divalent hydrocarbon radical, oxygen, or a divalent radical composed of carbon, hydrogen, and oxygen wherein the oxygen present is as an ether linkage. Among the acids containing aromatic ring-substituted carboxyl groups that are preferred are benzoic acid, phthalic acid, terephthalic acid, isophthalic acid, diphenic acid, homophthalic acid, toluic acid, alpha-naphthoic acid, chlorobenzoic acid, salicylic acid, 1,2-(ethylenedioxy)dibenzoic acid, and 2,5-dimethylterephthalic acid. Mixtures (3/1) of iso- and terephthalic acid are especially preferred.

The phenols utilized for production of the esters are mono functional phenols which contain only one phenolic hydroxyl group. Generally these phenols will be those of six to 15 carbon atoms of the formula

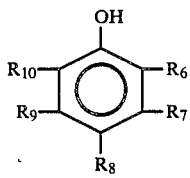

wherein $R_6$, $R_7$, $R_8$, $R_9$ and $R_{10}$ may be hydrogen, alkyl, alkaryl, aryl, or aralkyl radicals. Among the particular phenols that may be utilized are phenol, o-cresol, m-cresol, p-cresol, xylenols, either mixed or the pure isomer, o-phenylphenol, and p-phenylphenol. Of the various phenols that may be utilized, phenol itself is preferred over the others.

The reaction of the aromatic carboxylic acid with phenol in the presence of a catalyst is a known reaction which is carried out in the liquid phase in a customary manner using equipment normally used for esterfication reactions. The organic carboxylic acid is reacted with an excess of the phenol, usually a three to fourfold excess, based on the amount of dicarboxylic acid, in order to form a solution of the ester in the phenol after completion of the esterification reaction. The reaction conditions can be varied depending upon the type of esters being formed and the particular phenol being employed. A temperature sufficient to effect esterification in the presence of the catalyst is used and generally at temperatures ranging between 230° C. and 300° C.

The following examples illustrate the best mode now contemplated for carrying out the invention.

EXAMPLE 1

201 grams of crude diphenyl phthalate (a mixture of iso- and terephthalates in 3/1 ratio prepared with titanium butoxide catalyst) having an acid number of 3.5, 4.0 grams $B_2O_3$ and 1.3 grams $K_2CO_3$ were charged to a distillation system consisting of a 0.5 liter round-bottomed flask, 45 cm Vigreaux column (2.5 cm diameter) and air-cooled receivers. Heat is applied to the reboiler via a heated salt bath. After removal of low boiling phenol, virtually all of the diphenyl ester distilled over at a temperature of 236°-238° C. under a pressure of 0.85 mm Hg. The molten distillate color was APHA 100. In the absence of $B_2O_3$, the molten distillate is APHA 300-500.

EXAMPLE 2

Crude diphenyl phthalate, a mixture of iso- and terephthalates in 3/1 ratio prepared with Tyzor TE catalyst (triethanolamine titanate chelate), was neutralized with $K_2CO_3$ as in Example 1 and mixed with 0.2 wt. % $B_2O_3$. The mixture was flash distilled to yield a diphenyl ester product having an APHA color of 100. In the absence of $B_2O_3$ the color of the distillate was 200.

What is claimed:

1. A method for purifying a crude phenolic ester of an aromatic dicarboxylic acid which comprises distilling said ester under subatmospheric pressure in the presence of a boron oxide compound at temperatures ranging from about 225° C. to 260° C. to reduce color impurities thereof, and thereafter recovering a diphenyl ester having improved color properties.

2. The method of claim 1 wherein said esters are diphenyl phthalates and the boron compound is selected from the group consisting of $H_3BO_3$ and $B_2O_3$ 3. The method of claim 2 wherein the temperature ranges from about 230° C. to 250° C. and the pressure is 0.5-3 torr.

4. The method of claim 3 wherein said ester is a diphenyl phthalate which is prepared from the catalytic reaction of phenol with a 3/1 mixture of iso- and terephthalic acids.

* * * * *